United States Patent [19]

Othmer et al.

[11] Patent Number: 4,640,921

[45] Date of Patent: Feb. 3, 1987

[54] TREATMENT OF SEXUAL DYSFUNCTION WITH BUSPIRONE

[75] Inventors: Ekkehard Othmer; Sieglinde C. Othmer, both of Overland Park, Kans.

[73] Assignee: Bristol-Myers, New York, N.Y.

[21] Appl. No.: 825,826

[22] Filed: Feb. 4, 1986

[51] Int. Cl.⁴ .................. A61K 31/50; A61K 31/495
[52] U.S. Cl. .................................................... 514/252
[58] Field of Search ........................................ 514/252

[56] References Cited

U.S. PATENT DOCUMENTS

| | | | |
|---|---|---|---|
| 3,717,634 | 2/1973 | Wu et al. | 260/308 R |
| 3,976,776 | 8/1976 | Wu et al. | 514/252 |
| 4,182,763 | 1/1980 | Casten et al. | 514/252 |
| 4,438,119 | 3/1984 | Allen et al. | 514/252 |

OTHER PUBLICATIONS

Wu, et al., *J. Med. Chem.*, 15, 477-479 (1972).
Allen, et al., *Arzneim. Forsch*, 24, No. 6, 917-922 (1974).
Sathananthan, et al., *Current Therapeutic Research*, 18/5, 701-705 (1975).
Kurtz, et al., U.S. Ser. No. 791,182.
Slag, et al., JAMA, 249/13, 1736-1740 (1983).
Story, *J. Sex Research*, 10/2, 132-149 (1974).
Mitchell, et al., *Am. J. Psychiatry*, 139/5, 633-637 (1982).
Molcan, *Act. Nerv. Super*, 10/3, 261-262 (1968) (English translation attached).

*Primary Examiner*—Stanley J. Friedman
*Attorney, Agent, or Firm*—Richard P. Ryan; Robert H. Uloth

[57] ABSTRACT

Buspirone and its pharmaceutically acceptable salts are useful in treating patients of both sexes suffering from sexual dysfunction.

8 Claims, 1 Drawing Figure

TREATMENT OF SEXUAL DYSFUNCTION WITH BUSPIRONE

FIELD OF THE INVENTION

This invention is concerned with a drug bioaffecting and body-treating process which employs the pyrimidine compound 8-[4-[4-(2-pyrimidinyl)-1-piperazinyl]-butyl]-8-azaspiro[4.5]decane-7,9-dione or a pharmaceutically acceptable acid addition salt thereof (class 424, subclass 251).

BACKGROUND OF THE INVENTION

The pyrimidine compound with which the present invention is concerned has the following structural formula

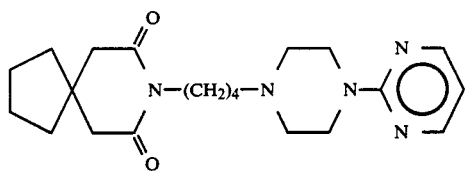

and is known as buspirone. The hydrochloride salt has been referred to in the prior art as MJ 9022-1 and as buspirone hydrochloride. Other acid addition salts thereof are named by combining "buspirone" with the appropriate word to define the acid from which it is prepared as in "buspirone hydrochloride". The latter is the United Stated Adopted Name (USAN); refer to *J. American Med. Assoc.* 225, 520 (1973).

The synthesis of the compound and the disclosure of its psychotropic properties are described in the following patents and publications.

1. Y. H. Wu, et al., *J. Med. Chem.*, 15, 477 (1972).
2. Y. H. Wu, et al., U.S. Pat. No. 3,717,634 which issued Feb. 20, 1973.
3. L. E. Allen, et al., Arzneim. Forsch., 24, No. 6, 917–922 (1974).
4. G. L. Sathananthan, et al., *Current Therapeutic Research*, 18/5, 701–705 (1975).
5. Y. H. Wu, et al., U.S. Pat. No. 3,976,776, issued Aug. 24, 1976.

The use of buspirone hydrochloride as a novel antianxiety agent for the treatment of neurotic patients is described in G. P. Casten, et al., U.S. Pat. No. 4,182,763, issued Jan. 9, 1980. Currently, a New Drug Application (NDA) is pending before the U.S. Food & Drug Administration for the use of buspirone in the treatment of anxiety neurosis.

Buspirone has also been disclosed as being useful in alleviation of of extrapyramidal motor disorders in U.S. Pat. No. 4,438,119, which was issued Mar. 20, 1984, to Allen, et al.

Currently, other clinical studies are being conducted to provide support for the use of buspirone in panic disorders. This use of buspirone was disclosed in U.S. Ser. No. 791,182, which is presently pending.

The present invention can be distinguished from the above prior art in that it is directed to a patient population which is characterized by a disease state different from that related to general anxiety disorder, panic disorder, or extrapyramidal motor disorders. Descriptions of these three different disease states may be found in the text of the above-cited references. While patients may suffer from sexual dysfunction concurrent with one of the above anxiety or movement disorders, nonetheless, these are clearly different disease states. To indicate the magnitude of the problem of sexual dysfunction, it has been estimated that a disturbance of sexual functions affects 34% of medical out-patients above the age of 35 (cf: Slag, et al., "Impotence in Medical Clinical Outpatients", JAMA, 249 (13): 1736–1740 (1983)).

While it is recognized that psychiatric disorders such as depression, alcoholism, neuroses and psychoses can interfere with sexual functions; most psychotropic agents further impair erectile and orgasmic ability (cf: Story, "Sexual Dysfunction Resulting From Drug Side Effects", *J. Sex Research*, 10(2): 132–149 (1974); Mitchell, et al., "Antipsychotic Drug Therapy and Sexual Dysfunction in Man", *Am. J. Psychiatry*, 139(5): 633–637 (1982)).

A report disclosing the use of mesoridazine, a phenothiazine antipsychotic agent, in treatment of male sexual

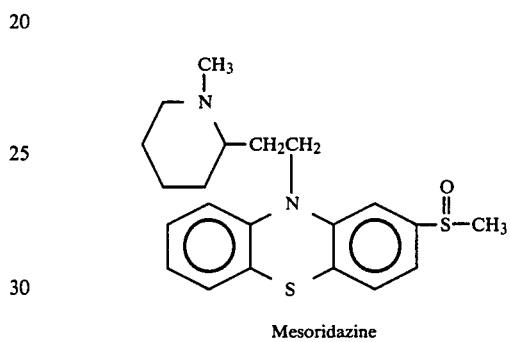

Mesoridazine function appeared in 1968 in the Czechoslovakian journal, *Act. Nerv. Super.* 10/3, pages 261–262. Mesoridazine, which is not structurally related to buspirone, is highly sedating and seemed mainly to affect premature ejaculation.

In summary, there exists nothing in the prior art which would teach or suggest that buspirone and its pharmaceutically acceptable salts would be useful in treatment of sexual dysfunction in both sexes.

SUMMARY OF THE INVENTION

The process of the present invention is intended for treatment of sexual dysfunction. The process essentially involves administration of buspirone, or a pharmaceutically acceptable acid addition salt thereof, to one in need of such treatment. For use in the instant process, oral administration of buspirone hydrochloride from about 10 to 60 mg per day in divided doses is anticipated as being the preferred dosage regimen. Pharmaceutically acceptable acid addition salts of buspirone and methods of pharmaceutical formulation are described in the above patents of Wu, et al., U.S. Pat. No. 3,717,634 and Casten, et al., U.S. Pat. No. 4,182,763, which are incorporated herein in their entirety by reference.

DETAILED DESCRIPTION OF THE INVENTION

Figure 1:
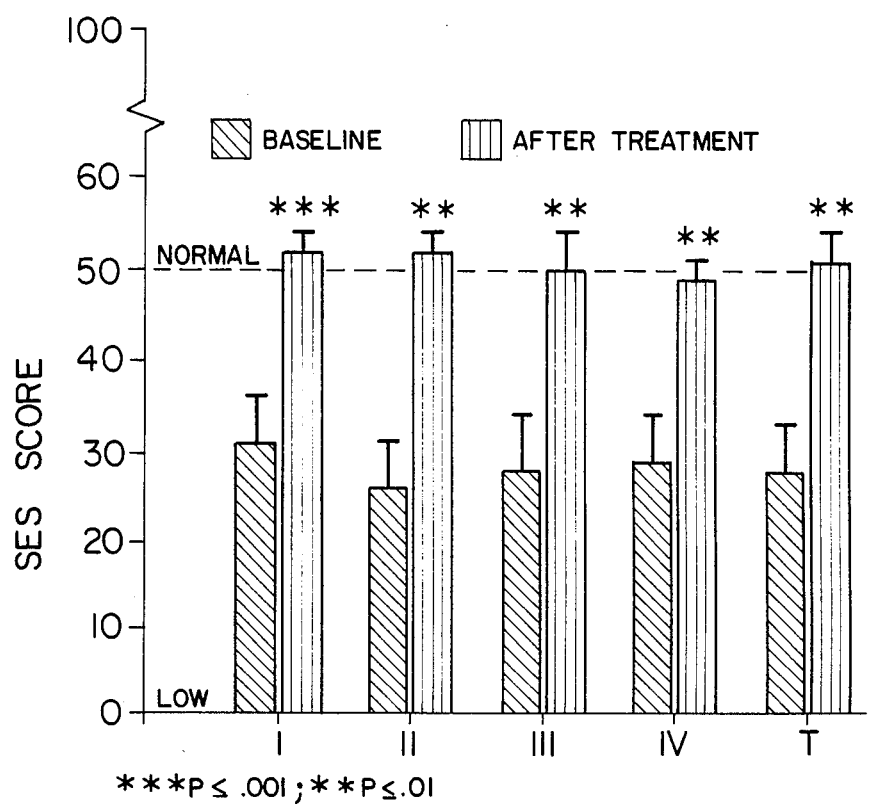
FIG. 1 graphically demonstrates improvement of sexual function in four factors of the Sexual Evaluation Scales (SES) measuring sexual interest (I), arousability (II), performance (III), seeking of sexual contact (IV), and total score (T). The comparative measurements on a scale of 0 to 100 were obtained at baseline (crosshatched bars) and after four weeks of buspirone treatment (vertical hatched bars). Scores are depicted using a 100 mm analog bar scale with scores around 50 representing normal functioning. Scores below 50 represent increasing hyposexuality and scores above 50 represent increasing hypersexuality.

Sexual functioning in men and women may be divided into three phases. The first phase depends on a mental state of anticipation which is also known as the sexual motive state or a state of desire. The second phase is that of arousal and is characterized by erection in the male and lubrication in the female. The third phase is that of performance and deals with the dimensions of orgasm. Disorders of sexual function can result with inhibition in the response cycle which may occur at one or more of the above sexual response phases or their components. In general, sexual dysfunction involves both the subjective parameters of sexual functioning, e.g. desire, arousal, and pleasure; as well as the objective parameters, e.g. performance, vasocongestion, and orgasm. Occasionally though, either the subjective or objective set of parameters may be solely involved in sexual dysfunction. Sexual dysfunction may also be classified as being primary which refers to life long, with effective performance never having been experienced in any situation; or secondary which relates to dysfunctions acquired after a period of normal functioning. Sexual dysfunction may also be further characterized as being generalized or limited to certain situations or with certain partners; and total or partial degree or frequency of disturbance.

The etiology of sexual dysfunction can comprise psychologic factors, interpersonal and situational causes, physical factors, and pharmacologic agent side effects. Since sexual dysfunction can result from a variety of these underlying causes which may range from purely psychogenic to completely physical, it would be unrealistic to expect a single treatment modality to be effective in all cases. In current medical practice, sexual dysfunction is usually treated by determining the underlying cause or causes and then treating them whenever possible. In many cases, identification of the underlying causes of either male or female sexual dysfunction is very complex or else cannot be determined with certainty. The psychopharmacologic treatment of sexual dysfunctioning is at present in its infancy. The use of pharmacologic agents in the treatment of sexual dysfunction has achieved little success as is evidenced by the absence of any recognized accepted pharmacologic treatment for this use. Anecdotal reports, however, of the use of various agents, compositions and formulations abound. Amphetamine, L-DOPA, and cocaine are examples of drugs that have been ascribed anecdotally as stimulating the libido. While reports of beneficial drug effects on sexual function are mainly anecdotal, a considerable literature deals with sexual dysfunction associated with drug treatment. In general, these effects are considered to be undesirable side effects from any of many medications including inter alia psychotropic agents.

It has now been found that buspirone can normalize sexual function in patients suffering from hyposexuality. This unexpected finding resulted from a study of patients having Generalized Anxiety Disorder in which sexual function was also measured by means of a psychometric instrument known as the Sex Evaluation Scales (SES). The SES is a rating instrument which is designed to measure drug- and illness-related changes in four dimensions of sexual functions: interest, arousal, performance and sexual contact seeking. The SES comprises 16 analog scales which are scored to measure sexuality in terms of 16 items (only 14 apply to females) which can be combined into the four factors. Each item is scored on a 100 mm analog bar with scores around 50 mm representing normal functioning. Scores below 50 represent increasing hyposexuality and scores above 50 represent increasing hypersexuality.

The SES as a rating instrument satisfies the following criteria:

1. Measures 4 clinical dimensions (sexual interest, arousal, performance and sexual contact seeking) as confirmed by factor analysis.
2. Shows retest reliability with $\geq 0.80$ for these four factors.
3. Reflects clinical conditions, i.e. differentiates between psychiatric patients and normal subjects.

The individual scale items, the four factors, and retest reliability are shown in Table 1.

TABLE 1

Sexual Evaluation Scales: Factors, Scale Items and Retest Reliability

| | Retest Reliability |
|---|---|
| Factors | |
| I SEXUAL INTEREST (scales 1-3 and 6-7) | .89 |
| II AROUSAL (scales 8-9 and 11) | .80 |
| III PERFORMANCE (scales 12-15) | .94 |
| IV SEXUAL CONTACT SEEKING (scales 4-5) | .88 |
| Scales | |
| 1. Less/more interest in sex | .80 |
| 2. *Paying less/more attention to opposite sex | .82 |
| 3. Seeking fewer/more sexual contacts | .61 |
| 4. Having fewer/more contacts | .78 |
| 5. Less/more frequent erotic fantasies | .59 |
| 6. Interested less/more in erotic literature | .89 |
| 7. Interested less/more in erotic movies | .84 |
| 8. More/less difficult to have an erection/be aroused | .82 |
| 9. Less/more frequent erections/arousals | .68 |
| 10. **More/less difficult to keep an erection | .90 |
| 11. Erections/arousal by touch only/before being touched | .80 |
| 12. More/less effort to have orgasm | .77 |
| 13. More/less time to reach orgasm | .85 |
| 14. Less/more intense orgasms | .91 |
| 15. More/less frequent orgasms | .83 |
| 16. **More/less difficult to control ejaculation | .85 |
| TOTAL | .92 |

*same sex if homosexual
**male only scales

Ten out-patients comprised of both males and females and suffering from Generalized Anxiety Disorder were tested for sexual function by using the SES prior to a four-week treatment regimen with buspirone. At the termination of the four-week drug treatment period the sexual function of the patient group was again measured with the SES. Other tests to measure anxiety had also been administered to the patients at baseline and at the end of weeks 1 through 4.

Only one patient of the ten patients had a normal sexual function score at baseline. After the four weeks of buspirone treatment, eight of nine dysfunctional patients had normal sexual function scores. All the patients had been made aware that they were receiving active medication for the relief of anxiety but they were not aware that the drug might improve sexual function. The results, displayed in FIG. 1, show the patient group score on a comparative scale of 0 to 100 for each of the four factors (I-IV) of the SES and the total score (T) at baseline (hatched bars) and at the end of the four-week buspirone treatment period (black bars). SES scores approaching 50 are in the normal range with scores very much below or above representing hyposexuality and hypersexuality, respectively. As can be seen, buspirone treatment was not associated with the generation of hypersexuality in this patient group and thus can be considered a normalizing agent. In conventional fashion, the standard deviation and p-values are indicated in FIG. 1. The change in sexual dysfunction score from baseline to completion of drug treatment period is statistically significant for each factor as well as total score.

It should be emphasized that the improvement in sexual function score occurred in both sexes. Another important observation was that the improvement in sexual function score did not seem to directly correlate with anxiety reduction in this patient group. This latter observation might suggest that the normalization of sexual function seems to be independent of the anxiolytic effect of buspirone. Therefore, a major aspect of our invention is that buspirone is effective in treating hyposexuality. A related aspect of this invention is that buspirone, in contrast to other anxiolytics, should not impair sexual function in anxious patients with normal sexuality.

Administration of buspirone may be made by the parenteral, oral, or rectal routes. The oral route is preferred, however. A clinical dosage range for treatment of sexual dysfunction is expected to be about the same as that for anti-anxiety usage but can vary to some extent. In general, the expected amount of buspirone administered would be less than about 100 mg per day, generally in the 20 mg to 80 mg range, and preferably in the range of 30–60 mg per day. Since the dosage should be tailored to the individual patient, the usual practice is to commence with a dose of about 5 mg administered two or three times per day and then to increase the dose every two or three days by 5 mg at each dosage time until the desired response is observed or until the patient exhibits side effects. Single daily dosage may be applicable in some instances. The average dose of buspirone at the termination of the four-week treatment described in detail above was 45 mg±5.2 mg per day.

What is claimed is:

1. A method for treating sexual dysfunction which comprises administering a non-toxic therapeutically effective dose of buspirone or a pharmaceutically acceptable acid addition salt thereof to a patient in need of such treatment.

2. The method of claim 1 wherein buspirone hydrochloride is employed and dosage is by the oral route.

3. The method of claim 1 wherein hyposexuality is the specific sexual dysfunction afflicting said patient.

4. The method of claim 1 wherein the patient is also afflicted with generalized anxiety disorder.

5. The method of claim 3 wherein the patient is also afflicted with generalized anxiety disorder.

6. The method of claim 2, 3, 4, or 5 wherein said patient is an adult and a daily dose of from about 10 mg to 60 mg of buspirone hydrochloride is employed.

7. The method of claim 6 wherein said daily dose is divided and administered b.i.d.

8. The method of claim 6 wherein said daily dose is divided and administered t.i.d.

* * * * *

UNITED STATES PATENT AND TRADEMARK OFFICE
CERTIFICATE OF CORRECTION

PATENT NO. : 4,640,921

DATED : February 3, 1987

INVENTOR(S) : Ekkehard Othmer; Sieglinde C. Othmer

It is certified that error appears in the above—identified patent and that said Letters Patent is hereby corrected as shown below:

On Cover Sheet,

[73] Assignee:

(i.e. assignee should be deleted).

Signed and Sealed this

Sixth Day of October, 1987

Attest:

DONALD J. QUIGG

Attesting Officer

Commissioner of Patents and Trademarks